United States Patent
Gu et al.

(10) Patent No.: US 7,955,483 B2
(45) Date of Patent: Jun. 7, 2011

(54) CARBON NANOTUBE-BASED GLUCOSE SENSOR

(75) Inventors: Yuandong Gu, Plymouth, MN (US); Barrett E. Cole, Bloomington, MN (US)

(73) Assignee: Honeywell International Inc., Morristown, NJ (US)

(*) Notice: Subject to any disclaimer, the term of this patent is extended or adjusted under 35 U.S.C. 154(b) by 1074 days.

(21) Appl. No.: 11/144,292

(22) Filed: Jun. 3, 2005

(65) Prior Publication Data

US 2005/0265914 A1 Dec. 1, 2005

Related U.S. Application Data

(63) Continuation-in-part of application No. 10/100,440, filed on Mar. 18, 2002, now Pat. No. 6,919,730.

(51) Int. Cl.
*C12Q 1/26* (2006.01)
*C12Q 1/54* (2006.01)

(52) U.S. Cl. ......... 204/403.04; 204/403.13; 204/403.14; 205/777.5

(58) Field of Classification Search .......... 204/400, 204/403.01–403.13; 205/775–778; 324/96, 324/715, 724; 422/82.01–82.13
See application file for complete search history.

(56) References Cited

U.S. PATENT DOCUMENTS

| | | | |
|---|---|---|---|
| 4,822,566 A * | 4/1989 | Newman | 422/82.01 |
| 5,283,438 A | 2/1994 | Dautriche | |
| 5,296,120 A * | 3/1994 | Bennett et al. | 204/196.33 |
| 6,046,485 A | 4/2000 | Cole et al. | |
| 6,090,545 A * | 7/2000 | Wohlstadter et al. | 435/6 |
| 6,096,497 A * | 8/2000 | Bauer | 435/4 |
| 6,097,138 A | 8/2000 | Nakamoto | |
| 6,140,045 A | 10/2000 | Wohlstadter et al. | |
| 6,400,088 B1 | 6/2002 | Livingston et al. | |
| 6,445,006 B1 | 9/2002 | Brandes et al. | |
| 6,485,913 B1 | 11/2002 | Becker et al. | |
| 6,919,730 B2 | 7/2005 | Cole et al. | |
| 7,057,402 B2 | 6/2006 | Cole et al. | |
| 7,282,329 B2 * | 10/2007 | Manalis et al. | 435/6 |
| 2002/0029979 A1 * | 3/2002 | Freund et al. | 205/775 |
| 2002/0123227 A1 * | 9/2002 | Winningham et al. | 438/700 |
| 2002/0197724 A1 * | 12/2002 | Noronha et al. | 436/95 |
| 2003/0068432 A1 * | 4/2003 | Dai et al. | 427/58 |

(Continued)

FOREIGN PATENT DOCUMENTS

JP 2001-264284 * 9/2001

OTHER PUBLICATIONS

Sotiropoulou, Sofia; Chaniotakis, Nikolas, Carbon Nanotube Array-Based Biosensor, 2003, Anal Bioanal Chem, 375, 103-105.*

(Continued)

*Primary Examiner* — Nam X Nguyen
*Assistant Examiner* — Bach T Dinh
(74) *Attorney, Agent, or Firm* — Schwegman, Lundberg & Woessner P.A.

(57) ABSTRACT

The present invention provides a sensor, such as a biosensor, comprising at least one self-assembled monolayer (SAM) comprising analyte-sensitive groups, such as glucose-sensitive groups, attached to the surface of the outer wall of a carbon nanotube (CNT), such as a single-walled carbon nanotube (SWNT), by terminal groups, which bind to a thin layer of a metal or metal oxide, which has been deposited on the surface of the outer wall of the nanotube.

25 Claims, 4 Drawing Sheets

U.S. PATENT DOCUMENTS

| | | | | |
|---|---|---|---|---|
| 2003/0081463 | A1* | 5/2003 | Bocian et al. | 365/200 |
| 2003/0082444 | A1* | 5/2003 | Kuhr et al. | 429/149 |
| 2005/0126913 | A1* | 6/2005 | Burke et al. | 204/547 |
| 2005/0244811 | A1* | 11/2005 | Soundarrajan et al. | 435/4 |
| 2006/0003438 | A1* | 1/2006 | Engstrom et al. | 435/287.2 |
| 2006/0228723 | A1* | 10/2006 | Bradley et al. | 435/6 |
| 2006/0254909 | A1* | 11/2006 | Kubo et al. | 204/403.01 |

OTHER PUBLICATIONS

Ajayan, P. M., "Nanotubes from Carbon", *Chem. Rev., 99*, American Chemical Society,(Jan. 5, 1999),1787-1799.

Cao, A., et al., "Tandem Structure of Aligned Carbon Nanotubes on Au and its Solar Thermal Absorption", *Solar Energy Materials & Solar Cells*, vol. 70 (4), Elsevier Science Publishers, Amsterdam, NL,(Jan. 1, 2002),481-486.

Collins, Philip G., et al., "Extreme Oxygen Sensitivity of Electronic Properties of Carbon Nanotubes", *Science*, v. 287 (Mar. 2000),1801.

Dai, H., et al., "Nanotube Molecular Wires as Chemical Sensors", *Science*, v. 287, (Jan. 2000),622.

Kataura, H., et al., "Optical Properties of Singlewall Carbon Nanotubes", *Synthetic Metals*, vol. 103, Elsevier Sequoia, Lausanne, CH,(1999),2555-2558.

Kong, J., et al., "Nanotube Molecular Wires as Chemical Sensors", *Science*, vol. 287, American Association for the Advancement of Science, US,(Jan. 28, 2000),622-625.

Lee, S. M., et al., "Hydrogen Adsorption and Storage in Carbon Nanotubes", *Synthetic Metals*, v. 113, (2000),209.

Varghese, O. K., et al., "Gas Sensing Characteristics of Multi-Wall Carbon Nanotubes", *Sensors and Actuators B*, vol. 81 (1), Elsevier Sequoia, S.A., Lausanne, CH,(Dec. 15, 2001),32-41.

Xu, J. M., "Highly Ordered Carbon Nanotube Arrays and IR Detection", *Infrared Physics & Technology*, vol. 42 (3-5), 1) Elsevier, NL 2) Workshop on Quantum Well Infrared Photodetectors, Dana Point, CA,(Jun.-Oct. 2001),485-491.

"U.S. Appl. No. 10/100,440, Amendment and Response filed Jan. 7, 2004 to Non-Final Office Action mailed Oct. 7, 2003", 12 pgs.

"U.S. Appl. No. 10/100,440, Amendment and Response filed Nov. 17, 2004 to Non-Final Office Action mailed Aug. 18, 2004", 13 pgs.

"U.S. Appl. No. 10/100,440, Amendment and Response filed Jun. 7, 2004 to Final Office Action mailed", 14 pgs.

"U.S. Appl. No. 10/100,440, Final Office Action mailed Apr. 7, 2004", 6 pgs.

"U.S. Appl. No. 10/100,440, Non-Final Office Action mailed Oct. 7, 2003".

"U.S. Appl. No. 10/100,440, Non-Final Office Action mailed Aug. 18, 2004", 5 pgs.

"U.S. Appl. No. 10/100,440, Notice of Allowance mailed Mar. 14, 2005", 7 pgs.

"U.S. Appl. No. 11/032,470, Amendment and Response filed Nov. 9, 2005", 7 pgs.

"U.S. Appl. No. 11/032,470, Non-Final Office Action mailed Aug. 10, 2005", 6 pgs.

"U.S. Appl. No. 11/032,470, Notice of Allowance mailed Jan. 30, 2006", 6 pgs.

"U.S. Appl. No. 11/032,470, Response filed May 13, 2005 to Restriction Requirement mailed Apr. 14, 2005", 4 pgs.

"U.S. Appl. No. 11/032,470, Restriction Requirement mailed Apr. 14, 2005", 5 pgs.

"European Application Serial No. 06844124.5, Office Action mailed Apr. 26, 2008", oar-4mo, 16.

"European Patent Application No. 03741755.7, Communication dated Nov. 21, 2005", 6 pgs.

"European Patent Application No. 03741755.7, Communication/Examination Report dated Sep. 7, 2006", 4 pgs.

"European Patent Application No. 03741755.7, Main Request and Auxiliary Request filed Mar. 13, 2008", 16 pgs.

"European Patent Application No. 03741755.7, Response filed Oct. 27, 2006 to Communication dated Sep. 7, 2006", 7 pgs.

"European Patent Application No. 03741755.7, Response filed Mar. 10, 2006 to Communication dated Nov. 21, 2005", 4 pgs.

08005838.1, "European Application No. 08005838.1 filed on Mar. 17, 2003, titled "Carbon Nanotube Sensor" (unpublished)", EESR.

08005837.3, "European Application No. 08005837.3 EP Search Report Jun. 12, 2008", 9 pgs.

08005837.3, "European Application Serial No. 08005837.3, Office Action mailed Feb. 11, 2009".

08005838.1, "European Application Serial No. 08005838.1, Office Action mailed Feb. 11, 2009", 19.

Collins, P. G, et al., "Extreme Oxygen Sensitivity of Electronic Properties of Carbon Nanotubes", *Science*, vol. 287 (5459), (Mar. 10, 2000), 1801-1804.

"Chinese Application Serial No. 200680027729.1, Office Action mailed on May 17, 2010", 3 pgs.

"Chinese Application Serial No. 200680027729.1, Response filed Oct. 7, 2010 to Office Action mailed on May 17, 2010", (w/ English Translation of Pending Claims), 7 pgs.

"European Application Serial No. 03741755.7, Summons to Attend Oral Proceedings dated Sep. 24, 2007", 7 pgs.

"European Application Serial No. 08005837.3, Response filed Jun. 11, 2009 to Office Action mailed Feb. 11, 2009", 10 pgs.

"European Application Serial No. 08005838.1, Response filed Jun. 11, 2009 to Office Action mailed Feb. 11, 2009", 10 pgs.

"European Application Serial No. 08005837.3, Summons to Attend Oral Proceedings mailed Oct. 6, 2010", 5 pgs.

"European Application Serial No. 08005838.1, Summons to Attend Oral proceeding mailed Oct. 6, 2010", 6 pgs.

Chung, W.-Y., et al., "Thermal and gas-sensing properties of planar-type micro gas sensor", Sensors and Actuators B, 64(1-3), (Jun. 1, 2000), 118-123.

Yan, G., et al., "An experimental study on high-temperature metallization for micro-hotplate-based integrated gas sensors", Sensors and Actuators B, 86(1), (Aug. 30, 2002), 1-11.

\* cited by examiner

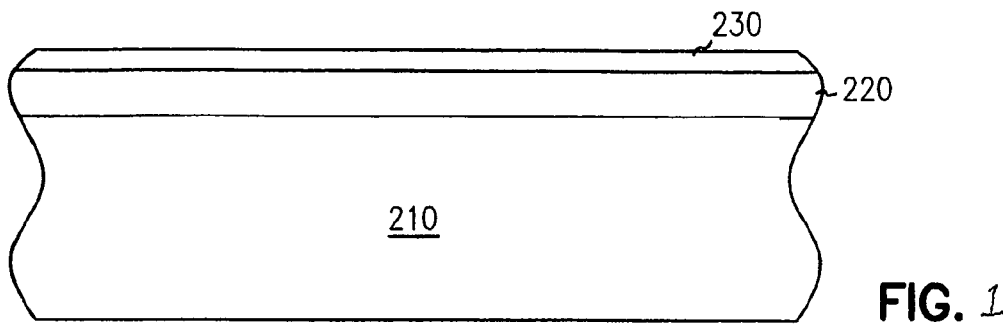
FIG. 1 A
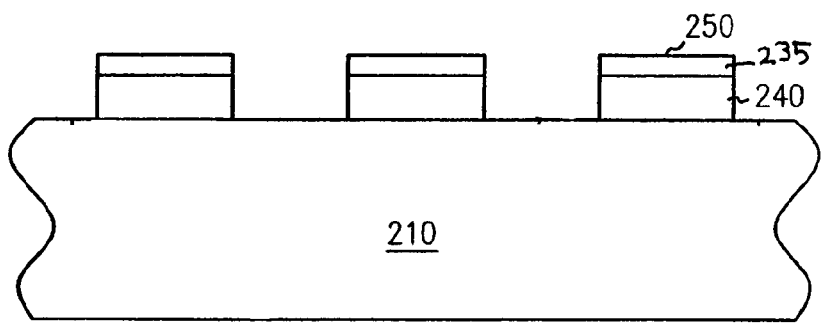
FIG. 1 B
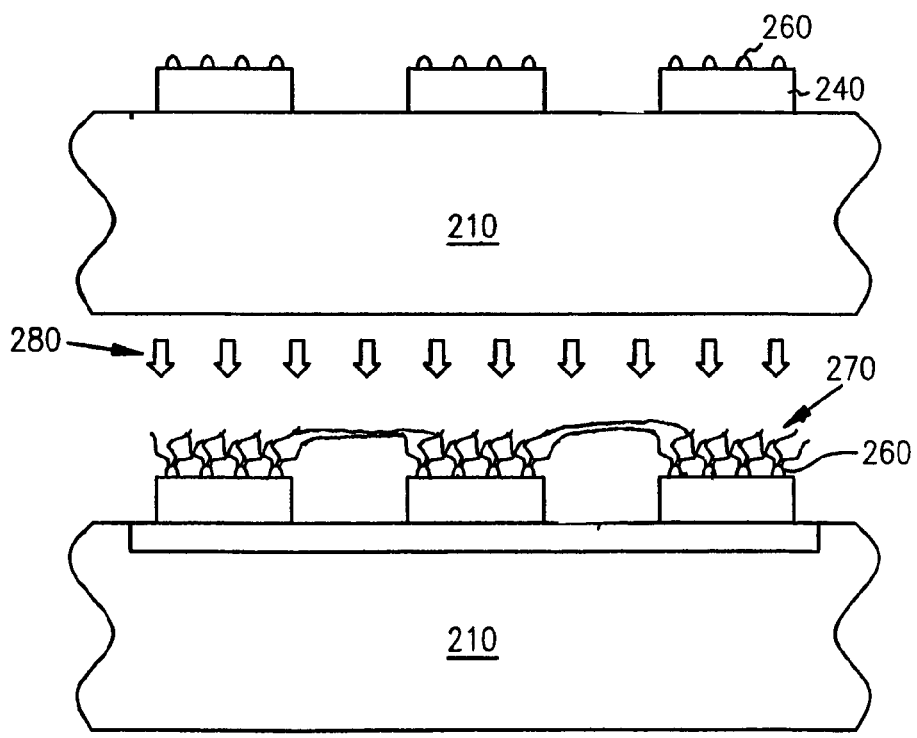
FIG. 1 C
FIG. 1 D

↓ HS-(R)-(X)

CARBON NANOTUBE-BASED GLUCOSE SENSOR

This application is Continuation-In-Part of U.S. patent application Ser. No. 10/100,440, filed on Mar. 18, 2002, now U.S. Pat. No. 6,919,730 the specification of which is incorporated herein by reference.

BACKGROUND OF THE INVENTION

Glucose detection in blood and urine is necessary for the diagnosis of diabetes. Glucose monitoring in fermentation of food industry is also necessary since the amount of glucose in the fermentation greatly influences the quality of the food products. See G. Harsanyi, "Sensors in Biomedical Applications: Fundamentals, Technology and Applications," Technomic Pub., Lancaster, Pa. (2000)). Glucose oxidase (GOD) has been widely used in glucose biosensors due to its high selectivity for glucose and high activity over a broad range of pH values. See B. J. White et al., *Biochem. Biophys. Res. Commun.*, 296, 1069 (2002). Sensitivity and stability of a glucose biosensor are key features for its quantitative analysis applications. See, e.g., V. G. Gavalas et al., *Analyt. Chim. Acta*, 67, 404 (2000); M. Delvaux et al., *Biosens. Bioelectron.*, 18, 943 (2003). Many attempts have been made to improve the features of the biosensors, including making use of novel immobilization techniques and new enzyme immobilization materials. Glassy carbon (GC), graphite, carbon paste, carbon fibers, porous carbon, and carbon spheres are commonly used as electrode materials for biosensor immobilization matrices (M. Albareda-Sirvent et al., *Sens. Actuat.*, B69, 153 (2000); S. Sotriropoulou et al., *Biosens. Bioelectron.*, 18, 211 (2003). Some GOD sensors do exhibit high sensitivity. However, the lifetime of the biosensors is only a few weeks and the stability is low, thus limiting their utility in harsh environments. See Z. Liron et al., eds., Novel Approaches in Biosensors and Rapid Diagnostic Assays, Kluwer, Acad./Plenum Pub., NY (2001) at page 203.

Carbon nanotubes (CNTs) are a new type of carbon material that can be considered to result from folding graphene layers into carbon cylinders. CNTs can be composed of a single shell-single-walled nanotubes (SWNTs) or several shells-multi-walled nanotubes (MWNTs). See S. Iijima et al., *Nature*, 363, 603 (1993); S. Iijima, *Nature*, 354, 56 (1991). CNTs have attracted increasing interest for potential applications in electron field emitters, field-effect transistors, actuators, and gas sensors because of their special geometry and unique electronic, mechanical, chemical, and thermal properties. CNTs have been recognized as promising electrode materials. SWNTs are semiconductors that exhibit high mobility since all their atoms are located on the tube surface. Only recently, have CNTs been investigated as biosensors for glucose and DNA detection and their performance has been found to be much superior to those of other carbon electrodes in terms of reaction rate, reversibility, and detection limit. See, e.g., S. Sotriropoulou et al., *Anal. Bioanal. Chem.*, 375, 103 (2003); A. Guiseppe-Elie et al., *Nanotech.*, 13, 559 (2002); M. L. Pedano et al., *Biosens. Bioelectron.*, 18, 269 (2003); K. Bestman et al., *Nano Lett.*, 3, 727 (2003); M. Gao et al., *Synth. Metals* 137, 1393 (2003). However, their potential utility has been limited by the need to functionalize the surface of the tubes to a sufficient stability and density, either covalently or noncovalently, while not disrupting the nanotube π delocalized system.

Chen et al., *J. Amer. Chem. Soc.*, 123, 3838 (2001) immobilized the protein ferritin on SWNTs via a 1-pyrenebutanoic acid, succinimidyl ester linking group. The linking group was noncovalently adsorbed onto the walls of SWNTs by π-stacking. The amine groups on the protein reacted with the anchored succinimidyl ester to form amide bonds that can immobilize proteins or other molecules containing free $NH_2$ groups. However, Chen et al. did not report the electrical characteristics of the functionalized SWNTs.

K. Besterman et al., *Nano Lett.*, 3, 727 (2003) used the same linking group to bind the enzyme glucose oxidase, E.C1.1.3.4, on carbon nanotubes. They observed that immobilization of the enzyme decreased the conductance of the SWNTs. Using a standard reference electrode, the conductance of the functionalized SWNTs were found to be sensitive to changes in pH and to glucose concentration. However, to yield useful nanoscale biosensors, it will be necessary to increase the effective density of sensing molecules on the surface of the SWNTs.

V. M. Mirsky et al., *Biosensors & Bioelectronics*, 12, 977 (1997) reported that self-assembled monolayers of functionalized thiols could be assembled on gold electrodes and employed to immobilize antibodies to human serum albumin (HSA). Subsequent binding of HSA led to a decrease of the electrode capacitance. While promising for use in the fabrication of conventional electrodes, this approach has not been applied to fabricate nanosensors. Thus, a continuing need exists for methods to prepare durable, sensitive nanosensors for biological analytes.

SUMMARY OF THE INVENTION

The present invention provides a biosensor, such as a glucose sensor, comprising at least one self-assembled monolayer (SAM) comprising analyte-sensitive groups, such as glucose-sensitive groups, attached to surface of the outer wall of a carbon nanotube (CNT), such as a single-walled carbon nanotube (SWNT). For example, the self-assembled monolayer can be attached to the nanotubes by terminal thiol groups, which bind to a thin layer of a substrate for a SAM, such as a submonolayer of a metal such as gold, silver, copper or palladium, which has been deposited on the surface of the outer wall of the nanotube. As used herein, the term "submonolayer" refers to a layer of a conductive metal or alloy such as gold that preserves the conductive properties of the CNT, e.g., it is not continuous to the extent that it forms a conductive layer on the nanotube. If desired, a dielectric layer such as a thin layer of a metal oxide such as $Ta_2O_5/TiO_2$ or $SiO_2$ can be applied to the nanotube surface and either used to anchor a SAM via free hydroxyl groups or the gold monolayer can be applied thereto. Such a layer can be continuous or discontinuous, and about 1 Å to about 10μ in thickness.

The analyte sensitive groups can include biomolecules such as proteins, including antibodies, cytokines, antigens, receptors, and the like, as well as enzymes, e.g., glucose-sensitive biomolecules such as GOD. However, to maximize the sensitivity of the biosensor to analyte, analyte-sensitive groups are preferred that are not biomolecules such as peptides or nucleic acids. Such molecules include organic functional groups capable of chelating or binding covalently to the target analyte. In the case of glucose and other saccharides, such groups include phosphate, phosphonate and boronate (boronic acid) groups. As discussed below, when a hydrated —$B(OH)_2$ group binds to a molecule of glucose, H+ is liberated and the pH of a test solution will drop. The pH drop in turn will cause a detectable change in the conductance of the functionalized CNT, which can be measured by techniques known to the art. See, e.g., B. R. Azamian et al., *J. Amer. Chem. Soc.*, 124, 12664 (2002). The binding of glucose to a boronic acid group can also be determined by a internal fluorescence assay, as disclosed below.

DETAILED DESCRIPTION OF THE INVENTION

Figure 1E:
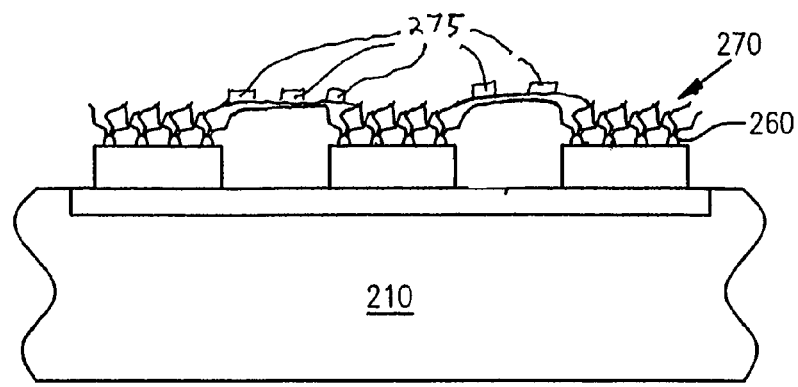
FIGS. 1(A-F) schematically depict formation of a biosensor of the invention.

In following description, reference is made to the accompanying drawings that form a part hereof, and in which is shown by way of illustration specific embodiments in which the invention may be practiced. These embodiments are described in sufficient detail to enable those skilled in the art to practice the invention, and it is to be understood that other embodiments may be utilized and that structural, logical and electrical changes may be made without departing from the scope of the present invention. The following description is, therefore, not to be taken in a limited sense, and the scope of the present invention is defined by the appended claims.

FIG. 1A-D are cross sectional representations illustrating formation of a glucose sensor. In this embodiment, a substrate 210 of silica has a first layer 220 formed, followed by a second layer 230. The first layer in one embodiment is platinum, or other layer having a higher melting point than the second layer 230. The second layer is nickel or cobalt, or other material on which carbon nanotubes will form.

Using common photolithographic techniques, several islands or platforms (250) are formed as shown in FIG. 2B. Each island is comprised of the first layer (240) and second layer (235) as earlier formed. Application of heat causes the formation of projections (260) out of the second layer material (235) as shown in FIG. 2C. The resulting structures form a desired pattern of platforms (240) having thin Ni islands (260) ready for carbon nanotube growth. In one embodiment, the platforms are 1-5 micron rectangles, with a 1-5 micron spacing. Both the size and spacing, as well as the projection density are easily modified.

In FIG. 2D, following application of heat (280) in an ethylene, methane or CO environment, nanotubes 270 have formed on and between the projections. Four point temperature probes are used in one embodiment to ensure proper temperatures are maintained for nanotube deposition. By modifying the size and spacing of the platforms, the density of the projections, and the quantity of nanotubes formed, conductivity between the island are modified. An electric field is applied to control the direction of growth of the CNTs, and to obtain point-to-point correction by the tubes. Since the platforms are formed of conductive materials, they can function as electrodes in the resulting biosensors.

A metal layer, such as a gold layer, can be provided as islands (275) as shown in FIG. 1E by sputtering a noncontinuous submonolayer of metal onto the CNTs (270). A self-assembled monolayer is then formed on the metal islands, which may have been further patterned as desired. The SAM (280) forms in a spontaneous, self-assembling process during which one end of the SAM component molecule end bonds covalently by complexation or by ionic association to the substrate surface, as by condensation with an oxide-, hydride-, halogen- or hydroxide-bearing surface of a substrate, such as the metal submonolayer or oxide, silicon hydride or silicon halide layer surface deposited on the CNT. Organic ligands that function as precursors to SAMs on the corresponding metallic or dielectric substrate layer are summarized on Table 1, below, where R includes those groups defined hereinbelow for HS—(R)—X.

TABLE 1

Ligands That Form Stable SAMs on the Corresponding Substrates

| Substrate | Ligand or precursor | Binding |
|---|---|---|
| Au, Ag, Cu | RSH, ArSH (thiols) | RS-M (M = Au, Ag, Cu) |
| Au | RSSR' (disulfides) | RS—Au, R'S—Au |
| Au | RSR' (sulfides) | RS—Au, R'S—Au |
| Au | $RSO_2H$ | $RSO_2$—Au |
| Pd | RSH, ArSH | RS—Pd |
| Pt | RNC | RNC—Pt |
| GaAs, InP | RSH | RS—GaAs, RS—InP |
| $SiO_2$, glass | $RSiCl_3$, $RSi(OR')_3$ | Siloxane |
| Si/Si—H | $(RCOO)_2$ (neat) | R—Si |
| Si/Si—H | $RCH=CH_2$ | $RCH_2CH_2Si$ |
| Si/Si—Cl | RLi, R—MgX | R—Si |
| Metal oxides | RCOOH | $RCOO^-\ldots MO_n$ |
| Metal oxides | RCONHOH | $RCONHOH\ldots MO_n$ |
| $ZrO_2$ | $RPO_3H_2$ | $RPO_3^{-2}\ldots Zr(IV)$ |
| $In_2O_3/SnO_2$ (ITO) | $RPO_3H_2$ | $RPO_3^{-2}\ldots M(n+)$ |

Efforts have been made to describe the arrangement and concentration of functional groups on the SAM surface. It is reasonably considered that the long-chain hydrocarbons project at a uniform, near-normal angle to the substrate, presenting an ordered close-packed two-dimensional array to their surroundings. See, e.g., J. Liu et al., *Chem. Phys. Lett.*, 303, 125 (1999). Monolayers of ω-functionalized thiols (280) can be adsorbed onto the gold, silver, copper, palladium, GaAs or InP "islands" by exposing the system to a solution of the appropriate sulfonic acid $RSO_2H$ or thiol, such as HS—(R)—X or disulfide X—(R)—S—S—(R)—X wherein each R is a $(C_2-C_{30})$alkyl, $(C_6-C_{14})$aryl, $(C_6-C_{14})$ar$(C_2-C_{30})$alkyl, $(C_2-C_{30})$alkaryl or $(C_2-C_{30})$alk$(C_6-C_{14})$ar$(C_2-C_{30})$alkyl linker, wherein alkyl is optionally interrupted by NH, N$(C_1-C_4)$alkyl, O, S, CH=CH, C≡C and the like. Organic isocyanides can react with Pt "islands" as shown on Table 1.

Alternatively, as shown on Table 1, the carbon nanotube surface can be provided with free hydroxy (OH) groups by application of a thin dielectric oxide layer, e.g., a $SiO_2$, $ZrO_2$, $In_2O_3/SnO_2$ or $Ta_2O_5$ layer, which can then be reacted with molecules of general formula $(R^1)_3Si$—(R)—X or $(HO)_2P(O)$—(R)—X wherein X and R are as defined above, and $R^1$ is halo (Cl, Br) or $O(C_1-C_4)$alkyl. These SAMs are strengthened by the formation of Si—O—Si or Ta—O—Ta bonds between the individual molecules, and can be a continuous monolayer or be several layers in thickness, or can be a discontinuous (submonolayer). Silicon substrate surfaces can react with organic peroxides or bind to X—(R)—CH=$CH_2$ via free radical addition of SiH groups, or via reaction of X—R—$SiCl_3$ or X—R—Si(OR')$_3$, wherein R' is $(C_1-C_4)$ alkyl, with free SiOH groups on $SiO_2$ surfaces, such as on glass. Organolithium or Grignard reagents can also couple with silicon hydride moieties as shown on Table 1. Also as shown on Table 1, a variety of metal oxides can bind to carboxylic acids, hydroxy amides and phosphonic acids.

X is a functional group that can either bind to the target analyte or be converted into such a binding group by further reaction. Such groups include halo, CN, $NH_2$, $SC(O)CH_3$, $PO_3H$, SCN, epoxy, vinyl, $CO_2(C_1-C_4)$alkyl, OH, $CO_2H$, $SO_3H$, $CO_2CF_3$, $C_6H_4B(OH)_2$, and $B(OH)_2$).

For immobilization of proteins, the acid and amino groups, such as ω-carboxy alkyl thiols and ω-amino alkyl thiols, can be activated to introduce phthalamido groups, succinimidyl groups, chlorocarbonyl, nitrophenyl, CHO, and NCS groups as taught, for example, by V. M. Mirsky et al., *Biosensors &*

*Bioelectronics,* 12, 977 (1997). Boronic acid and boronate terminated thiols can be prepared as disclosed in published U.S. patent application No. US-2003-0027982-A1, Kettner et al., *J. Biol. Chem.,* 259, 15106 (1984); and Matteson et al., U.S. Pat. No. 4,525,309.

The target substance may comprise a functional group reactive with a terminal functional group at the surface of the SAM, that is native to the target substance, e.g., as a boronic acid, an aldehyde or acetal group is to a sugar, or a $CO_2H$ or $NH_2$ group is to an amino acid, or the target substance may be modified to introduce a suitable functional group, e.g., by introducing avidin or biotin groups into a molecule to create a binding pair, or by introducing functional groups into an organic polymer such as a polymeric hydrocarbon or cellulose. The reaction and/or binding between the target substance and the SAM may be spontaneous upon contact of the two, or may be catalyzed or otherwise induced during the contact between the two materials. See, e.g., D. J. Pitchard et al., *Anal. Chem.,* 69, 3605 (1995), H. Gau et al., *Science,* 283, 46 (1999).

A preferred embodiment of the invention involves the formation of self-assembled monolayers by exposing the metal layer, such as a gold layer to a compound of general formulas HS—(R)—X wherein X is $B(OH)_2$ or $C_6H_4B(OH)_2$. In the presence of aqueous glucose, these compounds will react with glucose (Glu) or other diol-contained saccharide, to form a ketal-like derivative of general formula:

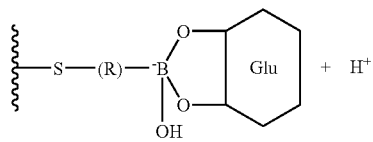

The liberation of $H^+$ lowers the local pH and alters the conductivity of the CNT. The rise or fall in conductivity can be detected and measured by methods known to the art.

Thus, one embodiment of the present invention employs compounds of formula I that form a self-assembled monolayer on a metal surface, such as a gold surface and that can fluoresce in the presence of saccharides:

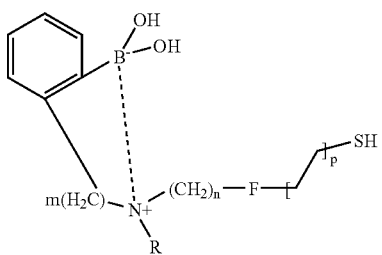

wherein F designates a fluorophore, R is a lower aliphatic or aromatic group, n and m are each 0, 1, or 2, n+m is the integer 2 or 3, p is 1 to 30, and the moieties $[CH_2CH_2]_p$ and the benzene ring attached to the boron atom is substituted or unsubstituted.

The compounds of formula I fluoresce in the presence of saccharides via a photoinduced electron transfer (PET) mechanism. The fluorescent intensity of the sensor changes in response to photoinduced electron transfer between the amine group and the fluorophore as modulated by the binding of saccharide hydroxyls to the boronic acid. In the absence of saccharide binding, the fluorescence by the fluorescent group is quenched by the unshared electron pair of the nitrogen atom. When glucose, for example, is bound, the unshared electron pair is utilized in the bond formation and does not participate in fluorescence-quenching. The formation of a boronate ester between boronic acid and glucose increases the Lewis acidity of boronic acid, decreases PET, and the intrinsic fluorescence of the sensor is reignited.

In the above formula I, the fluorophore (F) includes a number of atoms or groups containing $\pi$-electron systems. Preferred fluorophores include naphtyl, anthryl, pyrenyl, and phenanthryl groups. The most preferred fluorophore is anthryl. The fluorophore-forming atoms or groups are optionally substituted as long as the substituent(s) do not adversely affect the fluorescence.

In formula I, the R group attached to the nitrogen atom is a lower aliphatic ($C_1$-$C_6$) or aromatic functional group. Preferably, R is an alkyl group having 1 to 4 carbon atoms, i.e. methyl, ethyl, propyl, or butyl, or a phenyl group.

In formula I, m is 0, 1, or 2. Thus, the nitrogen atom in the compound of the present invention is disposed in the vicinity of the boronic acid moiety and the nitrogen atom is attached through a methylene group or an ethylene group, or is attached directly at the ortho position of the phenylboronic acid. Preferably m is 1, and thus the nitrogen is attached to the benzene ring via a methylene group. In formula I, n is also 0, 1, or 2, and n+m is the integer 2 or 3. Thus the nitrogen atom and the boronic acid are positioned proximate to the fluorophore. Preferably, n is 1.

The benzene ring attached to the boron atom of the phenylboronic acid may be substituted with an appropriate substituent or substituents as long as such substitution does not adversely affect the fluorescence. Examples of suitable substituents include methyl, ethyl, propyl, butyl, phenyl, methoxy, ethoxy, butoxy, and phenoxy groups.

The compound of the present invention as expressed by formula I contains a fluorophore in its molecular structure but does not emit fluorescence in the absence of saccharides. It is understood this is because the fluorescence of the fluorophore is quenched by the unshared electron pair of the nitrogen atom; the electron of the nitrogen occupies the lowest excited singlet energy state of the fluorophore so as to suppress the fluorescence. However, the compound of the present invention emits fluorescence of a high intensity upon binding to saccharides. This phenomenon may be accounted for as follows: the presence of saccharides produces a bond between the nitrogen atom(N) and the boron atom(B) to form a strong complex of the saccharide with the phenylboronic acid compound of the present invention, where the electron-deficient boron atom has been bound to the electron rich nitrogen. Thus, the unshared electron pair of the nitrogen atom has been utilized for bonding with the boron atom and will not contribute to the fluorescence-quenching electrogen transfer process, thereby expressing the intrinsic fluorescence of the compound.

A preferred compound falling within formula I of the present invention is the following compound of formula II, where F (the fluorophore) is anthryl, R is methyl and each of n, m, and p is 1.

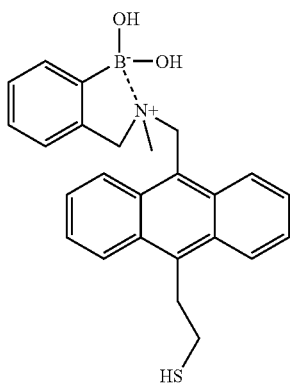

(II)

The compound of formula II exhibits fluorescence of a highly increased intensity in the presence of monosaccharides, such as D-glucose and D-fructose. Therefore, the compound is suitable for use in the detection of monosaccharides in general or a specific monosaccharide in particular. In the detection of a specific monosaccharide from a sample which may contain plural monosaccharides, the sample is generally subject to a pretreatment (e.g. a chromatography) for the separation of the monosaccharides, followed by the detection with the fluorescent compound of the present invention.

The compounds of the present invention form a self-assembled monolayer on the substrate surfaces shown in Table 1. For example, the thiol groups of the compounds I and II adsorb readily to a gold surface, thereby forming a monolayer comprising free phenylboronic acid moieties that act as saccharide binding sites. The thiols are adsorbed from a low-concentration solution thereof, preferably 0.5-2.5 mM, most preferably 1-2 mM. Suitable solvents include methanol, ethanol, and tetrahydrofuran (THF). The quality of the SAM is dependent upon the adsorption time. Suitable absorption times range from about 12 hours to two or three days. Longer absorption times are preferable for forming the highest quality SAMs.

The metal surface suitably is formed as a submonolayer film on the surface of a carbon nanotube such as a SWNT. Thin dielectric layers, such as metal oxide or silicon oxide layers can be continuous. Suitable substrate materials are those with good transmission of infrared, visible, and/or ultraviolet light.

Owing to the PET mechanism, in the absence of saccharide, the metal areas of the CNT covered by metal will not fluoresce; in the presence of saccharide, the metal surface will fluoresce. The PET property of the compounds of the present invention may vary depending upon the length of the alkylene chain attached to the thiol group.

Figure 1F:
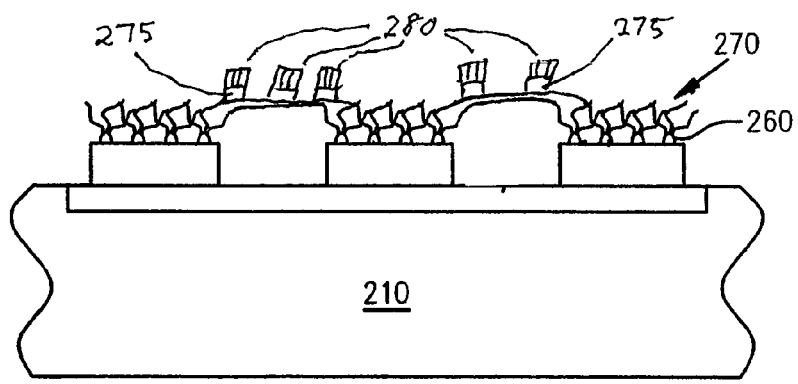

The construct of FIG. 1 may be implanted surgically into a patient for continuous monitoring of glucose levels. The fluorescence signal produced in the presence of glucose is then measured by optical means. If glucose is to be detected in an in vitro sample, i.e. a sample taken out of the living body of a patient, the fluorescence may be detected using a large-scale fluorescence detection unit or using a fluorescent detection microsystem, which also forms part of the present invention.

Since no lenses and mirrors are used in this optical system, strict alignment and spacing are not required in the assembly of the system. However, when an array of light sources is used, an alignment between the microchannel chip and the light-source may be necessary. When the light source is a chip, alignment is achieved by aligned silicon-glass anodic bonding or silicon-polymer-glass bonding.

The microsystem of the present invention offers many advantages compared to conventional optical detection systems. Conventional optical detection benches tend to be bulky and expensive. By contrast, the miniaturized system is less expensive, is compact, requires smaller amounts of samples, and is easy to use. These advantages are especially useful and important for self-monitoring of glucose by diabetic patients.

The invention will now be illustrated by the following non-limiting examples.

EXAMPLE 1

Preparation of 2-(9-(2-thioethyl)-1-(methyl-[methyl] amino) methyl)-phenylboronic acid (II)

Figure 2:
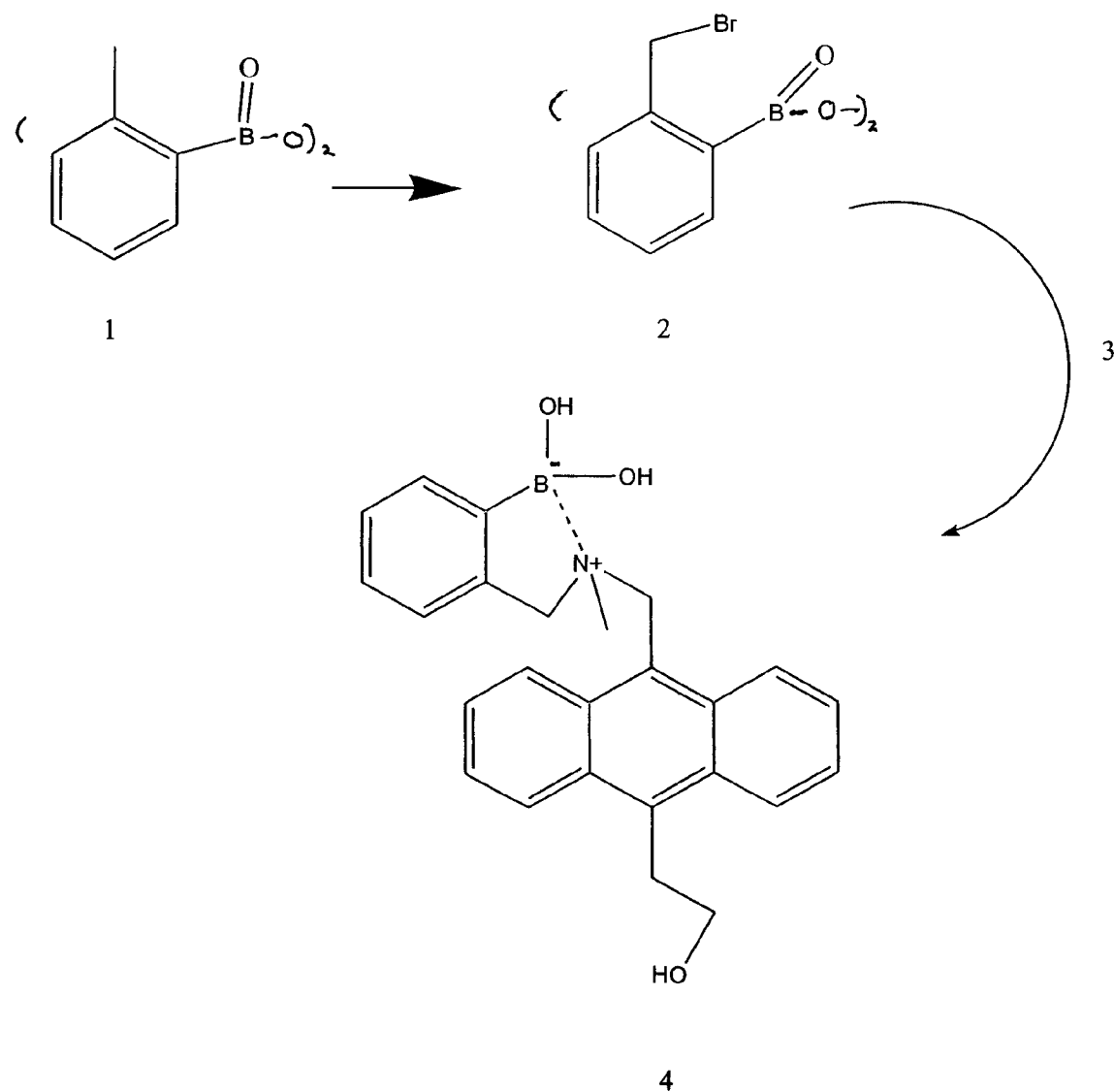
FIGS. 2 and 3 schematically depict the synthesis of compounds 4 and II, respectively.
Figure 3:
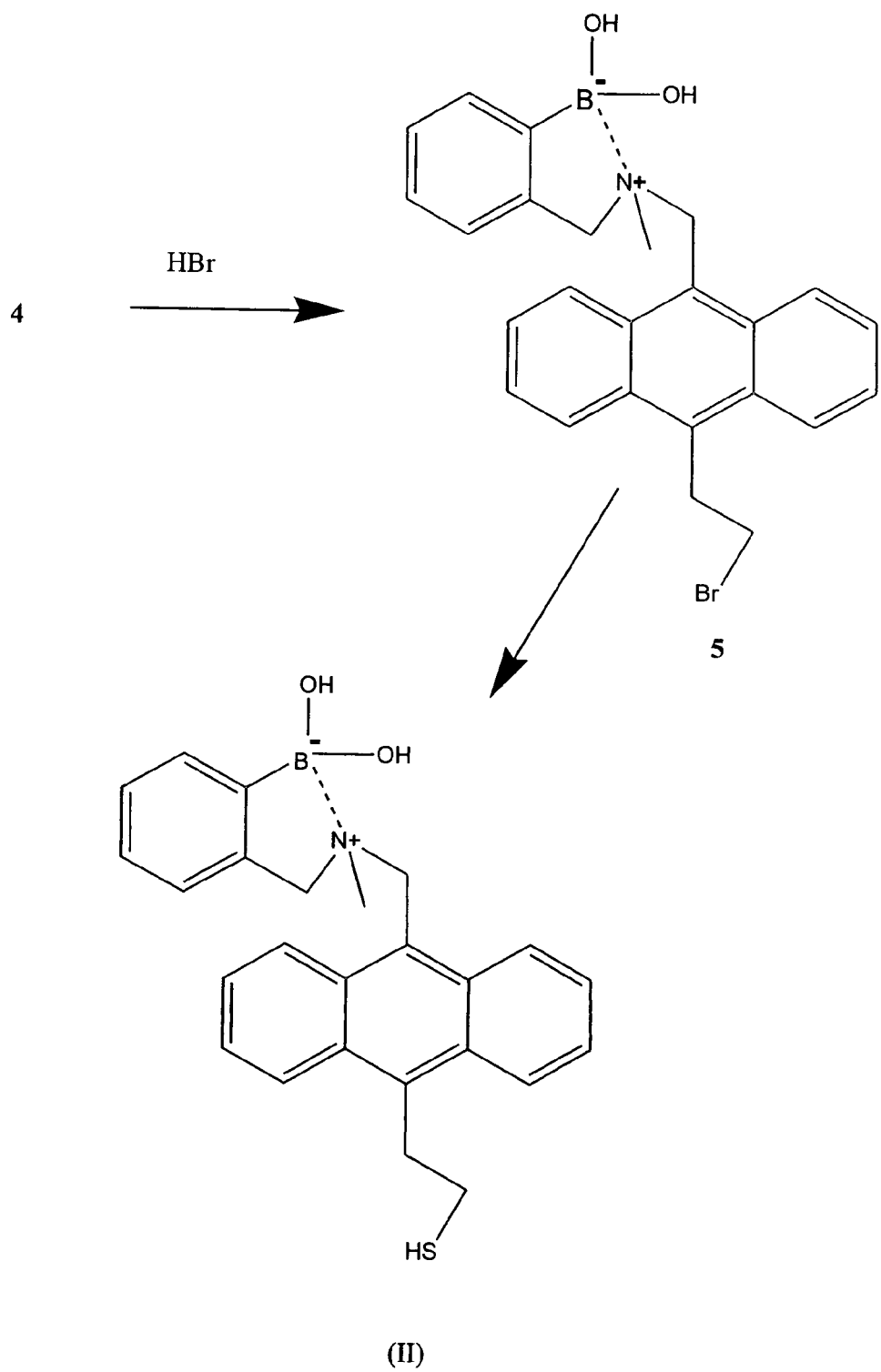

(2-bromomethyl)phenylboronic anhydride is prepared as follows: As shown in FIGS. 2-3, orthobromotoluene is reacted with magnesium (1.1 equivalents) in diethylether at 25° C. Grignard reagent is added dropwise to a solution of trimethylborate (10 equivalents) in diethylether at −78° C. The mixture is stirred further for 2 hours, then allowed to warm to room temperature, and stirred further for 2 hours. The diethylether is removed under reduced pressure, and the solid recrystallized from water. The product phenylboronic acid is dried in a vacuum oven overnight to produce phenylboronic anhydride (2).

The phenylboronic anhydride is mixed with NBS (N-bromosuccinimide) (1.1 equivalents) and catalytic AIBN (azoisobutylnitrile) in carbon tetrachloride as a solvent. The mixture is refluxed under radiation by a 200 Watt lamp for 2 hours. The solution is filtered when hot and the solvent removed to yield the 2-bromomethylboronic anhydride.

The bromomethylboronic anhydride is mixed with 9-methylaminomethyl-10-hydroxyethylanthracene (3) (2.1 equivalents) in chloroform and refluxed for 2 hours. The mixture is filtered when cool and the solvent is removed. The solid is then washed with diethylether and recrystallized from ethyl acetate, to give a product that is treated with a 25 percent excess of aqueous (48%) hydrobromic acid together with sulfuric acid. The mixture is refluxed for several hours. The water-insoluble layer is separated; washed successively with water, cold concentrated sulfuric acid, and sodium carbonate solution; separated; dried with calcium chloride; and distilled to give the corresponding bromide 2-(9-(2-bromoethyl)-1-methyl[(methyl)amino]methyl)-phenylboronic acid (5).

A mixture of 95% ethanol and thiourea is brought to reflux temperature on a steam bath. The steam is turned off and the bromide is added in one portion. Within 5 minutes a vigorous reaction ensues and the isothiuronium bromide salt of 5 separates from solution. The exothermic reaction is allowed to continue to completion without further application of heat. The isothiuronium bromide salt is collected by filtration and dried. A mixture of the isothiuronium bromide salt and 85% potassium hydroxide in water is boiled under reflux for 5 hours. The flask is then equipped with a separatory funnel, a gas-inlet tube, and a condenser for steam distillation. Nitrogen is admitted through the inlet tube, and a cooled solution of sulfuric acid in water is added dropwise. The addition is continued until the reaction mixture becomes acid to Congo red paper, and then a 20% excess of acid is added. At the end of the addition of acid, the passage of nitrogen is discontinued and steam is admitted through the inlet tube. The oil is separated from the water in the distillate and dried over calcium chloride. The crude product is fractionated through a 10-inch Vigreux column under reduced pressure in an atmosphere of nitrogen to yield the compound of formula II:

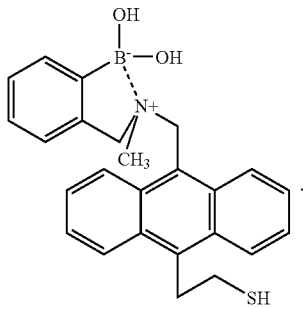

(II)

EXAMPLE 2

The self-assembled monolayer of the compound of formula II on a gold submonolayer on carbon nanotubes is prepared as follows.

A Superslip® microscope glass coverslip is used as the substrate of the nanotube chip. The coverslip is cleaned in Piranha solution (30% $H_2O_2$:concentrated $H_2SO_4$ 1:3) for 15 seconds and rinsed carefully with Milli-Q® grade water. The coverslip is then dried in a nitrogen stream and placed in a vacuum evaporator. A platinum film (about 50 nm thickness) is deposited on the coverslip using a Polaron E5000 sputter coating system and a nickel film is deposited onto the platinum film. The sputter coating system is maintained under conditions of $2.0 \times 10^{-2}$ mbar and 20 mA for 180 seconds.

The nickel and platinum films are then patterned to yield an interdigitated finger pattern represented by the islands 250 in FIG. 1B, and the nickel layer is annealed to form islands (260) as shown in FIG. 1D. Carbon nanotubes are then deposited so as to bridge the islands as shown in FIG. 1D. A submonolayer of gold is sputtered onto the assembly and the gold sputtered nanotubes are immersed in a solution of the compound of formula II for 15 hours. The concentration of the solution is 1.0 mM in THF:methanol 9:1 as solvent. The immobilization process is monitored by SPR spectroscopy. After SAM formation, the chip is rinsed with methanol and then dried under nitrogen.

Upon exposure to a dilute glucose solution the SAM assembly yields both a detectable light signal and a detectable change in conductance between adjacent electrodes.

REFERENCES

1. S. Takahashi, et al., *Analytical Sciences* 2004, 20, 757-759.
2. H. Murakami, et al., *Chemistry Letters* 2000, 940-941.
3. D. Huh, et al., Engineering in Medicine and Biology, 2002, 24th Annual Conference and the Annual Fall Meeting of the Biomedical Engineering Society EMBS/BMES Conference, 2002, Proceedings of the Second Joint Meeting, Volume 2, October 2002, 1642-1643.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to incorporate physically into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention.

The invention described illustratively herein suitably may be practiced in the absence of any element or elements, or limitation or limitations, which is not specifically disclosed herein as essential. The methods and processes described illustratively herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a detector" includes a plurality of such detectors, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also forms part of the invention. This includes the generic description of the invention with a proviso or negative limitation removing any subject matter from the genus, regardless of whether or not the excised material is specifically recited herein.

What is claimed is:

1. A micro-sized biosensor comprising:
   a micro-sized substrate;
   two or more conductive platforms, in contact with the substrate;
   a plurality of carbon nanotubes, in contact with the platforms and bridging the platforms sufficient to form a layer;
   a bonding layer, non-continuously positioned on the layer of carbon nanotubes; and
   a self-assembled monolayer (SAM) in contact with the bonding layer, the SAM comprising groups of the formula —R—X wherein R is an organic linking moiety containing a fluorophore and X is a binding moiety that, upon interaction with an analyte, gives rise to both a detectable light signal and alters the conductive properties of the plurality of carbon nanotubes, conductive platforms or both in an aqueous environment.

2. The micro-sized biosensor of claim 1 wherein the bonding layer is a submonolayer comprising gold, silver, copper, palladium, platinum, GaAs or InP.

3. The micro-sized biosensor of claim 1 wherein the SAM comprises an organic thiol.

4. The micro-sized biosensor of claim 1 wherein the bonding layer comprises gold and the SAM comprises organothio groups or organosulfonyl groups.

5. The micro-sized biosensor of claim 1 wherein the bonding layer includes a dielectric layer and comprises $SiO_2$ layer or a silicon layer that comprises Si—OH, Si—H or Si—Cl groups.

6. The micro-sized biosensor of claim 5 wherein R is bound directly to silicon atoms of the bonding layer.

7. The micro-sized biosensor of claim 5 comprising —Si—O—R—X groups.

8. The micro-sized biosensor of claim 5 wherein the SAM is formed by a process comprising reacting the bonding layer with X—R—$SiCl_3$, X—R—$Si(OR^1)_3$, (X—R—$CO_2)_2$, X—R—CH=$CH_2$, X—R—Li or X—R—MgX, wherein $R^1$ is ($C_1$-$C_4$) alkyl.

9. The micro-sized biosensor of claim 1 wherein the bonding layer is a metal oxide layer.

10. The micro-sized biosensor of claim 9 wherein the metal oxide layer is $Ta_2O_5TiO_2$.

11. The micro-sized biosensor of claim 9 or 10 wherein the SAM is formed by a process comprising reacting the bonding layer with X—R—$CO_2H$, X—C(O)NHOH or X—R—$PO_3H_2$.

12. The micro-sized biosensor of claim 1, 2, 5 or 9 wherein R is ($C_2$-$C_{30}$)alkyl, ($C_2$-$C_{30}$)alk($C_6$-$C_{12}$)aryl, ($C_6$-$C_{12}$)aryl ($C_2$-$C_{30}$) alkyl or ($C_2$-$C_{30}$)alk($C_6$-$C_{12}$)ar($C_2$-$C_{30}$)alkyl, wherein alkyl is optionally interrupted by NH, N($C_1$-$C_4$) alkyl, O, S, —CH=CH—, —C≡C— or combinations thereof.

13. The micro-sized biosensor of claim 1 wherein X is an enzyme.

14. The micro-sized biosensor of claim 1 wherein X is glucose oxidase and the analyte is glucose.

15. The micro-sized biosensor of claim 1 wherein X is —B(OH)$_2$ and the analyte is a saccharide.

16. The micro-sized biosensor of claim 1 wherein the plurality of carbon nanotubes comprise single-walled carbon nanotubes.

17. The micro-sized biosensor of claim 1, further comprising projections in contact with the platforms and the plurality of carbon nanotubes.

18. The micro-sized biosensor of claim 17, wherein the projections comprise nickel.

19. The micro-sized biosensor of claim 1, wherein the platforms function as electrodes.

20. The micro-sized biosensor of claim 1, wherein the SAM is represented by the formula (I);

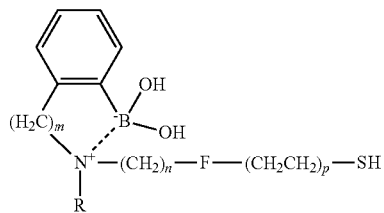

(I)

wherein F designates a fluorophore, R is a lower aliphatic or aromatic group, n and m are each 0, 1, or 2, n+m is the integer 2 or 3, p is 1 to 30, and the moieties [$CH_2CH_2$]$_p$ and the benzene ring attached to the boron atom is substituted or unsubstituted.

21. The micro-sized biosensor of claim 1, wherein the SAM (I) is represented by formula (II)

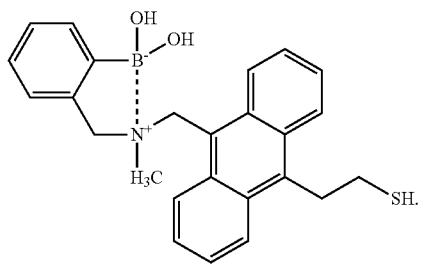

(II)

22. A method of detecting the concentration of glucose in an aqueous medium comprising contacting the micro-sized biosensor of claim 1 with an aqueous medium comprising glucose and measuring the change in the conductance or the fluorescence of the plurality of carbon nanotubes caused by the presence of glucose in the aqueous medium.

23. The method of claim 22 wherein the aqueous medium is water.

24. The method of claim 23 wherein the aqueous medium is blood or blood plasma.

25. A carbon nanotube having a 1Å to 10 μm layer of a substrate for a self-assembled monolayer (SAM) deposited on the outer surface thereof, and comprising, on said substrate, a SAM comprising groups of the formula —R—X wherein R is an organic linking moiety containing a fluorophore and X is a binding moiety that, upon interaction with an analyte, gives rise to a detectable signal and alters the conductive properties of the carbon nanotube when the nanotube is exposed to the substrate in an aqueous environment, characterized in that the substrate is a $SiO_2$ or a silicon layer that comprises Si—OH, Si—H, or Si—Cl groups.

* * * * *